United States Patent
Dumschat

[11] Patent Number: 5,837,199
[45] Date of Patent: Nov. 17, 1998

[54] MEASUREMENT APPARATUS FOR ANALYZING FLUIDS

[75] Inventor: Christa Dumschat, Münster, Germany

[73] Assignee: Institut Fur Chemo-Und Biosensorik Munster E.V., Munster, Germany

[21] Appl. No.: 615,192
[22] PCT Filed: Aug. 4, 1995
[86] PCT No.: PCT/DE95/01041
 § 371 Date: May 13, 1996
 § 102(e) Date: May 13, 1996
[87] PCT Pub. No.: WO96/04548
 PCT Pub. Date: Feb. 15, 1996

[30]   Foreign Application Priority Data

Aug. 5, 1994 [DE] Germany ................... 44 27 725.3

[51] Int. Cl.⁶ .................. G01N 27/00; G01N 21/00; G01N 33/00
[52] U.S. Cl. .................. 422/68.1; 128/635; 204/403; 204/416; 422/61; 422/82.01; 422/82.02; 422/82.03; 422/82.04; 422/82.05; 436/66; 436/68; 436/74; 436/79; 436/93; 436/96; 436/108; 436/110; 436/113; 436/150; 436/163
[58] Field of Search .................. 128/635; 204/403, 204/416; 422/61, 68.1, 82.01, 82.02, 82.03, 82.04, 82.05; 436/66, 68, 74, 79, 80–84, 93–99, 108, 110, 113, 150, 163

[56]   References Cited

U.S. PATENT DOCUMENTS

| | | | |
|---|---|---|---|
| 4,318,884 | 3/1982 | Suzuki | 422/63 |
| 4,339,317 | 7/1982 | Meiattini et al. | 204/195 B |
| 4,899,759 | 2/1990 | Pederson et al. | 128/693 |
| 5,046,496 | 9/1991 | Betts et al. | 128/635 |
| 5,114,859 | 5/1992 | Kagenow | 436/50 |
| 5,145,565 | 9/1992 | Kater et al. | 204/153.1 |
| 5,208,147 | 5/1993 | Kagenow et al. | 435/14 |
| 5,449,494 | 9/1995 | Seeney | 422/100 |

FOREIGN PATENT DOCUMENTS

| | | |
|---|---|---|
| 391634 | 11/1990 | Austria . |
| 0399227 | 11/1990 | European Pat. Off. . |
| 55-76639 | 6/1980 | Japan . |
| 55-144536 | 11/1980 | Japan . |
| 56-40748 | 4/1981 | Japan . |
| 58-115361 | 7/1983 | Japan . |
| 4-194660 | 7/1992 | Japan . |
| 9300994 | 1/1993 | WIPO . |

OTHER PUBLICATIONS

V. A. Knight *J. Appl. Physiol.* 1976, 40, 441–442.

Primary Examiner—Arlen Soderquist
Attorney, Agent, or Firm—Greenblum & Bernstein P.L.C.

[57]   ABSTRACT

The invention relates to a measurement apparatus (1) for analysing fluids, comprising a container (3) in the form of a syringe, into which a fluid may be taken in via an intake device (14) through at least one opening (5), and further comprising a sensor (7) which is either integrated in the container wall (9) or is attached to said container wall (9), the sensor(s) (7) being so disposed that it/they can come into contact with the fluid which may be taken up into the cavity (10).

28 Claims, 3 Drawing Sheets

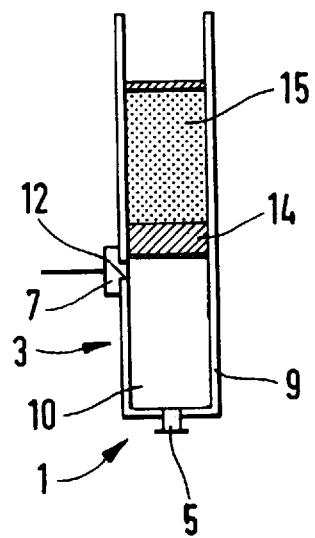
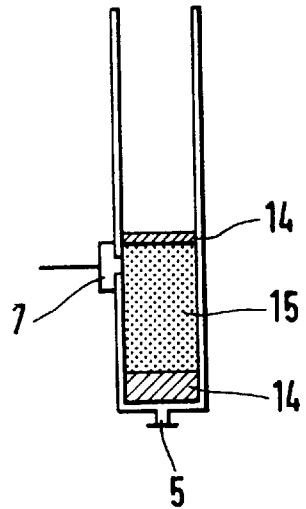
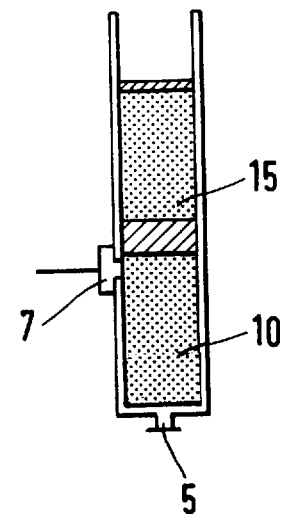

Inoperative Position

Sampling

Inoperative Position

Sampling

MEASUREMENT APPARATUS FOR ANALYZING FLUIDS

CROSS-REFERENCE TO RELATED APPLICATION

The present invention claims priority under 35 U.S.C.§119 of German Patent Application No. P 44 27 725.3.

BACKGROUND OF THE INVENTION

1. Field of the Invention

The invention relates to a measurement apparatus comprising a container in the form of a syringe into which a fluid can be taken up through at least one cannula as an intake device, a sensor being integrated in or on the wall of the container in such a way that it can come into contact with the fluid taken up into the cavity of the container. The invention further relates to the use of such a measurement apparatus.

2. Discussion of Background Information

In order to determine the concentrations in a solution of dissolved ions or molecules by means of chemical sensors, the solution to be investigated is removed from its point of origin, filled into an appropriate vessel, and measurement is undertaken by submerging the sensor.

Another measurement method operates according to the throughflow principle. In this case the solution for analysis flows past a sensor. For this purpose also the solution to be analysed is firstly removed and then passed over the sensor. A measurement principle of this type is described for example in J. Ruzicka, E. H. Hansen: Flow Injection-Analysis, New York, John Wiley Sous, 1981. Both these methods are only of restricted usefulness for on-site analysis, which is gaining importance in modern analysis, as they are too complex, and require qualified personnel. Analysis platelets or test strips were developed for these particular applications.

Analysis platelets are used by various commercially-available systems, especially for blood-testing (e.g. Kodak Ektachem DT II system, Kodak AG, Klinische Chemie, Postfach 60 03 45, Stuttgart). In this case blood is firstly removed, and the blood is applied by means of a pipette. Measurement is then undertaken.

A similar procedure takes place in measurement with electrochemical test strips.

Thus, for rapid on-site analysis, the sample is removed from its point of origin and applied to the sensor in a second step.

This method of operation is however disadvantageous for various analyses, particularly blood analyses, analysis of toxic and sensitive substances.

In the analysis of infectious analytical media, e.g. blood, it is possible, due to incautious operation with drops of blood, that infection may occur, or spillage of the sample. A further disadvantage is that an alteration in the concentration of the analytical subject is possible in an open drop of blood by evaporation or absorption of air components (e.g. alteration in the pH value). Finally, it is desirable in many cases to carry out a calibration before the actual measurement, principally because the one-time sensors used in the procedures described above cannot always be manufactured in a reproducible manner. Such calibration, however, is not possible with the methods described above.

The i-STAT sensor system (i-STAT Corporation 303A College Road East, Princeton) was developed as a solution to this problem. Here one-time sensors are located in a cartridge in a flow duct. A calibrating solution is located in a plastics bag in the cartridge. Calibration and measurement are effected in accordance with a complex measurement procedure. firstly the sample is filled into the forward region of the flow duct by capillary action. Then the plastics bag is destroyed by pressure of a spike on the cartridge. The calibrating solution flows over the sensor. Next the sample is passed over the sensor by pressure on the cartridge. This measuring system permits rapid on-site analysis of concentrations, but is expensive because of its complex structure. Moreover, the cartridge is not directly suitable for sampling.

SUMMARY OF THE INVENTION

Proceeding from this point, the object of the present invention is to propose a measurement apparatus by means of which it is possible to undertake a simple, cost-effective and reproducible on-site analysis. At the same time, precise measurement results are to be obtained with the measurement apparatus.

The present invention may be directed to a measurement apparatus for analyzing fluids. The measurement apparatus may include a container in the form of a syringe that includes a cavity. A plunger, including at least one reservoir, may be guided in the cavity for drawing fluid to be tested into the cavity through at least one cannula. The measurement apparatus may also include sensors located to contact a calibrating fluid and the fluid under test. The calibrating fluid may be located within the reservoir.

The present invention may also be directed to a measurement apparatus for analyzing a medium. The measurement apparatus may include a container including an opening, a cavity in fluid communication with the opening, and at least one sensor being one of integrated in and mounted on a wall of the container. The measurement apparatus may also include at least one plunge movably disposed in the cavity, the at least one plunger including at least one reservoir and a calibrating solution disposed in the at least one reservoir. The at least one plunger may be utilized for drawing the medium into the cavity through the opening, and the at least one reservoir and the at least one sensor may be arranged such that the calibrating solution and the medium in the cavity separately contact the at least one sensor.

The present invention may also be directed to a measurement apparatus for analyzing medium that includes a container having an opening, a cavity in fluid communication with the opening, and at least one sensor being one of integrated in and mounted on a wall of the container. The measurement apparatus may also include at least one plunger movably disposed in the cavity and a medium to be analyzed located in the cavity. The at least one plunger may include at least one reservoir and a calibrating solution disposed in the at least one reservoir. The at least one reservoir and the at least one sensor may be arranged such that the calibrating solution and the medium in the cavity separately contact the at least one sensor.

According to the invention, therefore, a measurement apparatus is proposed which comprises a container in the form of a syringe, into which a fluid, e.g. the solution to be analysed (analytical subject), may be taken in through at least one cannula, a sensor being integrated in or on the container wall, in such a way that it can come into contact with the analytical subject which can be taken into the container, so that a direct sampling is possible. According to the invention the container has at least one plunger containing a reservoir, into which a calibrating liquid may be filled. In this way the analytical subject may be taken directly into the container, and it is thus ensured that the analytical subject can be removed directly from its point of origin and passed to the sensor.

The essential factor in the apparatus according to the invention is the fact that the analytical subject may be taken in directly, and can come directly into contact with the sensor integrated in the container without interposed procedural steps. By virtue of the fact that the container is designed in the form of a syringe, the blood for example can thus be removed directly from a patient by induction with the syringe, and immediately passed to the container with the sensor located therein. Measurement is then undertaken either immediately or, as shown in the embodiments in FIGS. 2 and 3, after removal of the fluid and intermediate storage.

The essential factor in the subject-matter of the Application is that at least one plunger with a reservoir for receiving the calibrating solution is provided in the container. In this way simple, rapid, precise and reproducible measurement is possible. A similar procedure may be followed in all other applications, e.g. in air analysis by direct intake of the air, or with other liquids, e.g. water, by direct removal of the water by the measurement apparatus through the opening disposed in the container. Preferably, the measurement apparatus has a plunger including a reservoir, and a seal member likewise movable in the cavity. A second movable plunger, preferably with a reservoir, may be provided instead of the seal member. In this way it is possible to take in the fluid, and only to undertake evaluation later. In this case the cannula or cannula connection is so designed that the fluid can pass into the cavity resulting between the movable portions (plunger, and plunger or seal member). The cannula is therefore preferably passed through at least one plunger or the seal member. Another possible form is that in which the cannula or the cannula connection is passed through the container wall from the exterior.

In the measurement apparatus, it is preferable to locate the sensor(s) on the external surface of the container wall over an aperture which leads into the interior of the container. This embodiment of the invention is particularly preferred because it is extremely simple in terms of process and production engineering to mount it on containers known per se in prior art, i.e. providing apertures and attaching a sensor to its outer surface. The dimensions of the aperture depend on the sensor selected for the particular purpose. It requires only to be ensured that the active surface of the sensor, which is directed into the interior of the container cavity, seals the aperture off from the outside, so that none of the fluid which may be taken in can escape outwards. The sensor(s) is/are in this case so disposed that the fluid taken into the container can come into contact with the sensor. As it is desirable as a rule to analyse only relatively small quantities, the measurement apparatus is also selected so that the volume of the container lies in the range between 10 $\mu$l and 100 ml. In another advantageous embodiment, a sensor card containing one or more sensors may be processed directly into the syringe body, or the sensors may be produced by depositing various layers directly on the syringe body.

The selection of the sensor depends on the measuring problem to be solved. The measurement apparatus may basically be used for all sensors known per se from prior art, as long as they can be integrated into the container wall. Suitable sensors are for example ion-selective electrodes such for example as ion-selective electrodes for $NH_4^+$, $Ca^{2+}$, $H^+$, $Li^+$, $K^+$, $Na^+$, $NO_3^-$ or biosensors such for example as biosensors for urea or glucose, or amperometric sensors such for example as sensors for analysing oxygen or heavy metals. The sensors are preferably designed as one-time sensors.

The invention further relates to the use of the measurement apparatus described above for analysing liquids and gases. The measurement apparatus according to the invention is particularly suitable for blood analyses. In this case the measurement apparatus may be used for example to analyse blood electrolytes, glucose, urea or oxygen. Other appropriate uses are water analysis, in this case in particular the analysis of heavy metals, oxygen or pesticides. The measurement apparatus according to the invention may also be used for air analysis, e.g. for detecting CO, $CO_2$ or ammonia.

BRIEF DESCRIPTION OF THE DRAWINGS

Further features, details and advantages of the invention will be apparent from the description of the preferred embodiments of the invention, with reference to the drawings, which show:

FIG. 1a)–1c) the theoretical structure of the measurement apparatus according to the invention, the container being in the form of a syringe;

FIG. 1a–1c shows the embodiment of the invention in which the container is designed as a one-time syringe.

DETAILED DESCRIPTION OF THE INVENTION

Figure 2A:
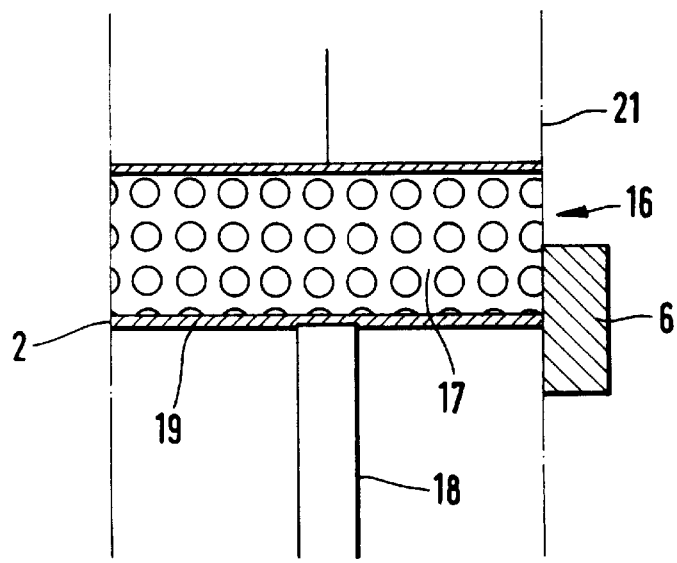
FIG. 2a)–2b) the theoretical structure with a plunger and a movable seal member, and FIG. 3a)–3b) the theoretical structure with two plungers.

The measurement apparatus 1 comprises a container 3 in the form of a syringe, provided with an opening 5 for intake of the fluid. A one-time syringe known from prior art, such as is used for medical purposes, may be used as a syringe. This syringe, known per se from prior art, is modified for the measurement apparatus 1 in that at a suitable point in the container wall 9 there is produced an aperture 12, and in that a sensor 7 is attached to the outer side of the container wall 9. In the example according to FIG. 1, the sensor is a potassium-sensitive sensor. The sensor is disposed over the aperture 12 in such a way that it seals the aperture 12 from the cavity 10. As an intake device, the measurement apparatus 1 has a plunger 14, which is provided with a reservoir 15. This development of the invention enables a calibrating solution to be filled into the reservoir 15. For this purpose there can be, in the outwardly-directed portion of the plunger 14, an opening through which the calibrating solution is filled. It is also possible to design the upper portion of the plunger 14 as a removable part. The sensor is now spatially located on the container wall 9 in such a way that, upon actuation of the plunger 15 in the direction of the opening 5, the active surface of the sensor comes into contact with the calibrating solution. This is shown schematically in FIG. 1b. Accordingly, for measurement, the plunger 14 is moved downwards out of its inoperative position (FIG. 1a). This state is shown in FIG. 1b. Now the sensor can be calibrated by means of the calibrating solution which is housed in the reservoir 15. In order to perform a measurement, the fluid, i.e. the analytical subject, is removed directly from its point of origin by a cannula (not shown) attached to the opening 5, and taken into the cavity 10 of the container 3 by movement of the plunger 14.

Thus there is made available a measurement apparatus which can pass the fluid to be investigated directly from its point of origin to the sensor without an interposed procedural step. It is particularly advantageous in the embodiment described above that it becomes possible simultaneously and in one procedural step to carry out a calibration and to take in the fluid, e.g. blood, to be investigated. The dimensions of the container depend on the medium to be investigated, and in the embodiment according to FIG. 1, comes to 0.5 ml. The syringe itself can consist of any previous materials such as have previously been used for syringes.

In order to evaluate the results obtained by the sensor it is possible on the one hand to connect the sensor directly to an evaluation unit, or to store the measurement values and then feed them separately to the evaluation unit.

Figure 2B:
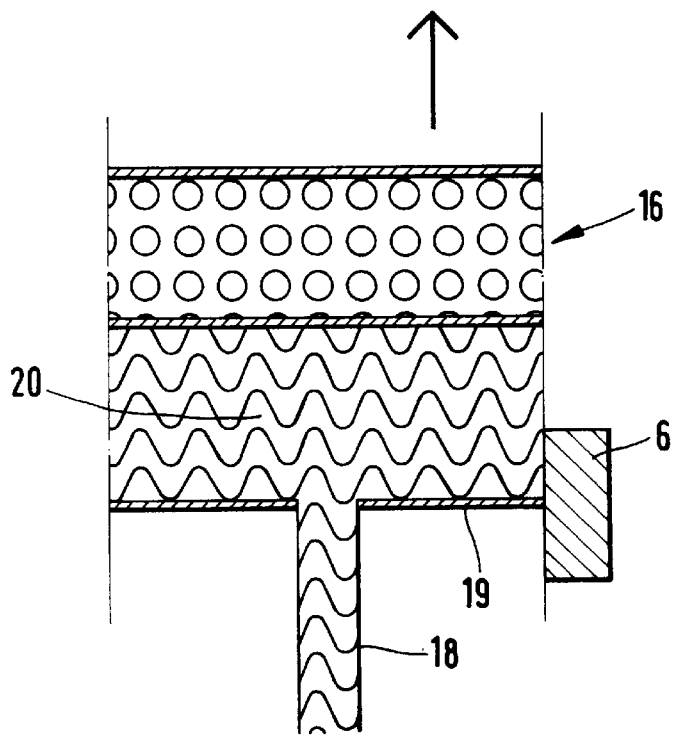

FIGS. 2a, 2b shows the theoretical structure of a measurement apparatus 2; in this case a plunger 16 is provided with at least one reservoir 17 and a seal member 19 with a cannula 18 integrated therein, said seal member being movable in the cavity 20 of the measurement apparatus 2 (FIG. 1a). The cannula 18 is closable, or removable and the connection is closable. This arrangement has the advantage that the fluid may be removed from the patient, and then evaluation of the measurement can be carried out on a separate measurement apparatus. In this case therefore the syringe need not be directly connected to the measurement apparatus during sampling, but may be intermediately stored.

Intake is undertaken in such a way that the movable plunger 16 is drawn upwards (in the direction of the arrow), so that the fluid collects in the resultant cavity 20. The syringe may now be intermediately stored along with the fluid thus filled, and may be measured at an appropriate moment on an external evaluation unit. FIG. 2 shows this condition. Measurement is carried out in such a way that the plunger 16 with the fluid located underneath in the cavity 20, and the seal member with the cannula 18, which is closed, are together moved past the sensor 6. In this case the sensor first comes into contact with the fluid, and then with the calibrating solution. Thus a precise and reproducible measurement is made possible. The position of the sensor 6 may be so selected that it comes into to contact with the calibrating solution while already in the inoperative position (FIG. 2a). This ensures that the sensor is already moistened, and later adapts better during measurement. Whether the sensor is already in contact with the calibrating solution while in the inoperative position or not, depends on the sensor to be used. There are sensors which are better stored in a moist condition (such for example as oxygen sensors and reference electrodes), and sensors which are better stored dry (e.g. ion-selective electrodes or biosensors). Thus positioning of the sensor is effected in dependence on the measurement problem faced.

In a variant of the embodiment in FIGS. 2a, 2b it is naturally also possible, instead of the seal member 19 with the cannula 18, to mount a second plunger which is likewise movably disposed in the cavity 20 of the measurement apparatus 2. In this case the cannula is passed through the plunger, so that then also the fluid can pass into the cavity 20. It is also possible, in order to enable movement of the seal member 19 or of a second plunger, to mount an additional device in the form of a web, such as is shown on the plunger 16, so that the movement of the second plunger or of the seal member may be reinforced.

By means of this second web, a further variant of the construction according to FIGS. 2a, 2b is possible, i.e. mounting the sensors above the plunger 16, then bringing them into contact with the fluid during intake of the measurement solution, and moving plunger, fluid and calibrating solution past the sensor for measurement. This has the advantage that, during the period between sampling and measurement, conditioning of the sensors with the calibrating solution takes place, leading to a shortened measurement time.

Figure 3A:
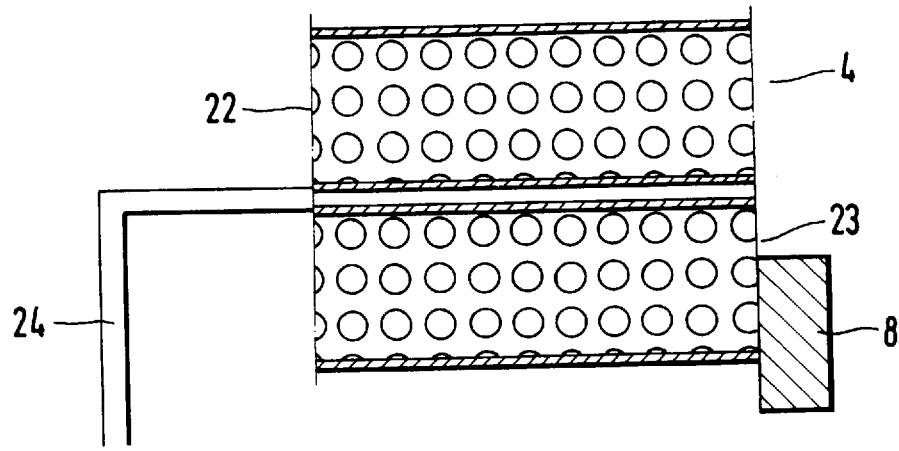
Figure 3B:
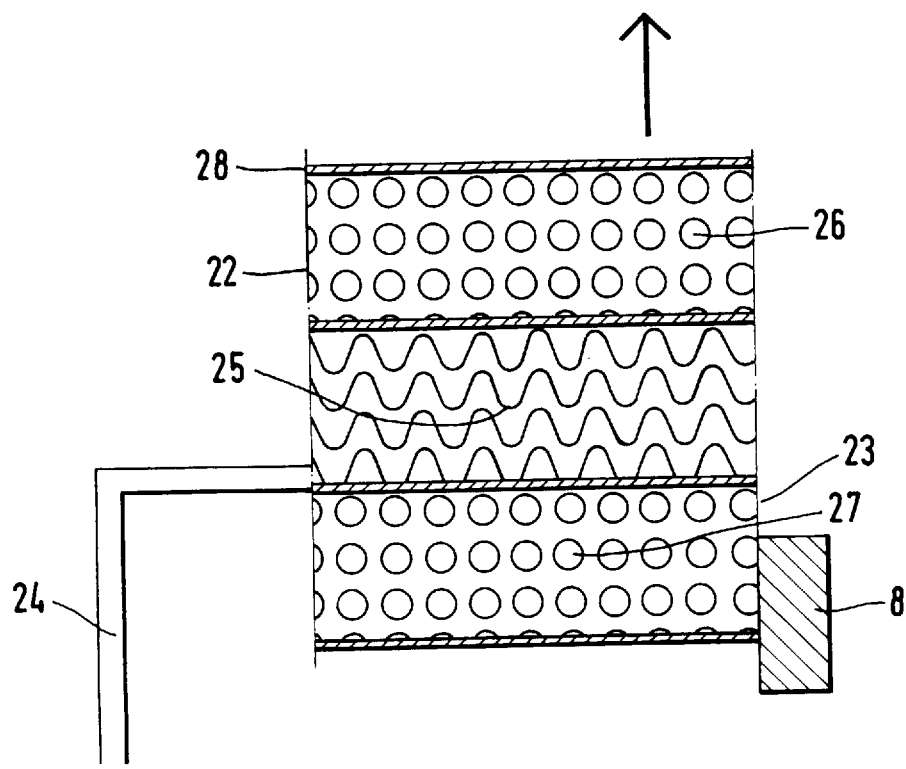

FIGS. 3a, 3b shows a further embodiment of the subject-matter of the invention, in that in this case a measurement apparatus 3 is provided with two movable plungers 22 and 23, each having a reservoir 26 and 27 respectively. The method of operation corresponds to that already described in FIG. 2.

In contrast to the embodiment in FIGS. 2a, 2b the cannula 24 is laterally flange-connected to the container wall 28. Sampling is again carried out in such a way that fluid is taken in through the cannula 24 by actuating the plunger 22. The fluid thus collects in the resultant cavity 25. In this position (FIG. 3b), the measurement apparatus can be again stored and then, as required, connected to the appropriate evaluation unit. Measurement again follows the procedure already described in FIG. 2. For this purpose the plunger 26 is pressed downwards, so that the calibrating solution of plunger 23 and the fluid in the cavity 25, as well as the calibrating solution in plunger 22, move past the sensor 8. Similarly to the embodiment in FIG. 2, it is also possible here for the second plunger 23 to be so constructed, either that it is correspondingly guided in the cavity 25 of the container 4, or that, in order to reinforce the movement, another additional web is provided. Here again, similarly to Example 2, it is also possible to dispose the sensors above the plunger 22, and to use the web, after removal of the fluid, to execute a movement of all the plungers and solutions from the top downwards, in this way moving the individual solutions past the sensor. In this way conditioning of the sensors with calibrating solution would again be possible between sampling and measurement. As already described in FIGS. 3a, 3b the cannula 24 may be closed off from the cavity 25. This enables secure transport and storage of the fluid.

What is claimed is:

1. A measurement apparatus for analyzing a medium, comprising:
    a container including an opening, a cavity in fluid communication with the opening, and at least one sensor being one of integrated in and mounted on a wall of the container;
    at least one plunger movably disposed in the cavity;
    the at least one plunger including at least one reservior;
    a calibrating solution disposed in the at least one reservoir;
    the at least one plunger for drawing the medium into the cavity through the opening; and
    the a least one reservoir and the at least one sensor arranged such that the calibrating solution and the medium in the cavity separately contact the at least one sensor.

2. The measurement apparatus according to claim 1, further comprising a seal member movably disposed in the cavity.

3. The measurement apparatus according to claim 1, the at least one plunger comprising two plungers movably disposed in the cavity.

4. The measurement apparatus according to claim 1, further comprising one of a cannula and a cannula closure in fluid communication with the opening.

5. The measurement apparatus according to claim 4, further comprising a seal member movably disposed in the cavity.

6. The measurement apparatus according to claim 5, the one of the cannula and the cannula closure being guidable through the seal member.

7. The measurement apparatus according to claim 4, the one of the cannula and the cannula closure being guidable from an exterior through the container wall into the cavity.

8. The measurement apparatus according to claim 4, the one of the cannula and the cannula closure being closable after removal of the one of the cannula and the cannula closure.

9. The measurement apparatus according to claim 1, further comprising:

an aperture in the container wall; and the at least one sensor being disposed in the apperture.

10. The measurement apparatus according to claim 1, the at least one sensor comprising a disposable sensor.

11. The measurement apparatus according to claim 1, the at least one sensor being selected from the group consisting of ion-selective electrodes, biosensors, aperometric sensors, optical sensors, and gas sensors.

12. The measurement apparatus according to claim 1, the least one sensor comprising and ion-selective electrode for detecting ions selected from the group consisting of $NH_4$, $Ca^{2+}$, $H^+$, $Li^+$, $K^+$, $Na^+$, and $NO_3^-$.

13. The measurement apparatus according to claim 1, at least one sensor comprising a biosensor for detecting analytes selected from the group consisting of urea, glucose, and pesticides.

14. The measurement apparatus according to claim 1, the at least one sensor comprising an amperometric sensor for detecting analytes selected from the group consisting of oxygen and heavy metals.

15. The measurement apparatus according to claim 1, the at least one sensor comprising a sensor for detecting analytes selected from the group consisting of blood electrolytes, glucose, urea, and oxygen.

16. The measurement apparatus according to claim 1, the at least one sensor comprising a sensor for detecting analytes selected from the group consisting of nitrates, heavy metals, oxygen, and pesticides.

17. The measurement apparatus according to claim 1, the at least one sensor comprising a sensor for detecting analytes selected from the group consisting of CO, $CO_2$, and $NH_3$.

18. The measurement apparatus according to claim 1, the container comprising a syringe.

19. A measurement apparatus according to claim 1, further comprising a medium to be analyzed being located in the cavity.

20. The measurement apparatus according to claim 19, the medium comprising at least one of a liquid and a gas.

21. The measurement apparatus according to claim 19, the medium comprising blood.

22. The measurement apparatus according to claim 19, the medium comprising water.

23. The measurement apparatus according to claim 19, the medium comprising air.

24. The measurement apparatus according to claim 19, the medium to be analyzed comprising at least one analyte selected from the group consisting of blood electrolytes, glucose, urea, and oxygen.

25. The measurement apparatus according to claim 19, the medium to be analyzed comprising at least one analyte selected from the group consisting of nitrates, heavy metals, oxygen, and pesticides.

26. The measurement apparatus according to claim 19, the medium to be analyzed comprising at least one analyte selected from the group consisting of CO, $CO_2$, and $NH_3$.

27. The measurement apparatus according to claim 19, further comprising a seal member movably disposed in the cavity.

28. A measurement apparatus for analyzing a medium, comprising:

a container including an opening, a cavity in fluid communication with the opening, and at least one sensor being associated with a wall of the container;

at least one plunger movably disposed in the cavity;

the at least one plunger including at least one reservoir; and a calibrating solution disposed in the at least one reservoir.

* * * * *